(12) United States Patent
Qin et al.

(10) Patent No.: US 11,628,315 B2
(45) Date of Patent: Apr. 18, 2023

(54) ULTRASOUND THERAPY SYSTEM

(71) Applicant: Women's Hospital School of Medicine Zhejiang University, Zhejiang (CN)

(72) Inventors: Jiale Qin, Zhejiang (CN); Jiang Zhu, Zhejiang (CN); Gonglin Fan, Zhejiang (CN)

(73) Assignee: WOMEN'S HOSPITAL SCHOOL OF MEDICINE ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 17/794,252

(22) PCT Filed: Jan. 6, 2021

(86) PCT No.: PCT/CN2021/070436
§ 371 (c)(1),
(2) Date: Jul. 20, 2022

(87) PCT Pub. No.: WO2021/147671
PCT Pub. Date: Jul. 29, 2021

(65) Prior Publication Data
US 2023/0059904 A1    Feb. 23, 2023

(30) Foreign Application Priority Data

Jan. 22, 2020  (CN) .......................... 202010075363.7

(51) Int. Cl.
*A61N 7/00*       (2006.01)
*C12M 1/34*       (2006.01)
(52) U.S. Cl.
CPC ............... *A61N 7/00* (2013.01); *C12M 41/46* (2013.01); *A61N 2007/0039* (2013.01)
(58) Field of Classification Search
CPC .. A61N 7/00; A61N 2007/0039; C12M 41/46
See application file for complete search history.

(56) References Cited

U.S. PATENT DOCUMENTS

2010/0158815 A1* 6/2010 Wang ................. A61B 8/481
                                                          424/9.52
2010/0178305 A1* 7/2010 Rapoport ............. A61K 31/513
                                                           977/788
(Continued)

FOREIGN PATENT DOCUMENTS

CN       102233159 A      11/2011
CN       102657612 A       9/2012
(Continued)

OTHER PUBLICATIONS

Polascik ed., "Imaging and Focal Therapy of Early Prostate Cancer," Current Clinical Urology, 273-282 (2013).
(Continued)

*Primary Examiner* — Hien N Nguyen
(74) *Attorney, Agent, or Firm* — Morgan, Lewis & Bockius LLP

(57) ABSTRACT

The present disclosure provides an ultrasound therapy system and a dose control method. The system includes: a control device; a first ultrasound irradiation device configured to generate multiple groups of ultrasound irradiation doses driven by the control device and conduct ultrasound irradiation on a cell culture device with multiple groups of abnormally proliferating living cells; a characterization image capture device configured to capture performance characteristic data of living cells in the cell culture device, where the control device is further configured to determine an ultrasound irradiation dose corresponding to at least one group of abnormally proliferating living cells with a cell target characteristic characterization as a target ultrasound irradiation dose according to the performance characteristic data; and a second ultrasound irradiation device configured to conduct ultrasound irradiation of the target ultrasound (Continued)

irradiation dose on a living organism with abnormal proliferation.

7 Claims, 12 Drawing Sheets

(56) References Cited

U.S. PATENT DOCUMENTS

2014/0335156 A1* 11/2014 Kosheleva ......... A61K 41/0033
424/178.1
2015/0125960 A1* 5/2015 Liaw ................. C12N 15/8207
435/471

FOREIGN PATENT DOCUMENTS

| CN | 107753466 A | 3/2018 |
|----|-------------|--------|
| CN | 110711323 A | 1/2020 |
| CN | 111167024 A | 5/2020 |

OTHER PUBLICATIONS

Liu et al., "Low-intensity focused ultrasound (LIFU)-induced acoustic droplet vaporization in phase-transition perfluoropentane nanodroplets modified by folate for ultrasound molecule imaging," International Journal of Nanomedicine, 12: 911-923 (2017).
Office Action issued in corresponding Chinese Patent Application No. 202010075363.7 dated Jan. 7, 2022.
Office Action issued in corresponding Chinese Patent Application No. 202010075363.7 dated Aug. 16, 2021.
Office Action issued in corresponding Chinese Patent Application No. 202010075363.7 dated Feb. 3, 2021.
Notice of Allowance issued in corresponding Chinese Patent Application No. 202010075363.7 dated Apr. 15, 2022.
International Search Report issued in corresponding International Patent Application No. PCT/CN2021/070436 dated Mar. 24, 2021.

* cited by examiner

ULTRASOUND THERAPY SYSTEM

CROSS REFERENCE TO RELATED APPLICATION

This application claims priority to the Chinese Patent Application No. CN202010075363.7, filed with the China National Intellectual Property Administration (CNIPA) on Jan. 22, 2020, and entitled "ULTRASOUND THERAPY SYSTEM AND DOSE CONTROL METHOD", which is incorporated herein by reference in its entirety.

TECHNICAL FIELD

The present disclosure relates to the technical field of inhibition of cancer cells, and in particular, to an ultrasound therapy system.

BACKGROUND ART

With the development of human tumor therapy, minimally invasive therapy with endoscopic technology is gradually replacing part of traditional surgical therapy, and non-invasive in-vitro therapy is optimal for therapy. For non-invasive cancer therapy, the doctor does not need to cut the skin and muscle of the patient and remove any tissue or organs. Such a therapy minimizes trauma to the body, potentially shortens postoperative recovery time for patients, and can be applied to patients who cannot be treated surgically. Such an approach may become an independent new method for tumor therapy, or an important part of a comprehensive therapy. Ultrasound therapy, as a non-invasive technology, uses an external ultrasound energy source to accurately locate the target tissue by coupling with the skin, such that a therapeutic effect can be achieved in the target area. It is expected to become a non-invasive therapy of solid tumors, which is another leap in the medical field.

Ultrasound tumor therapeutics mainly includes high-intensity focused ultrasound (HIFU) and low-intensity focused ultrasound (LIFU), which are based on a high-temperature effect. At present, HIFU has been applied in the treatment of clinical tumors and non-tumor diseases, and its principle of action is that high-energy ultrasound produces a high thermal effect in the focal area (instantly reaching 70-90° C.), which causes the thermal coagulation and necrosis of tissue proteins in the target area, resulting in a physical cell killing effect. However, HIFU exposes some safety limitations in clinical practice. For example, it is affected by rib movement or intestinal peristalsis during respiration, and the acoustic wave channel of high-energy ultrasound is offset or scattered, causing burns to adjacent organs. The safety can be improved by directly reducing ultrasound intensity.

In order to ensure a sufficient local therapeutic effect while reducing the ultrasound intensity, the synergy of microbubbles (MBs) is required. In the LIFU+MB therapy system, MB refers to lipid, protein or polymer-encapsulated gas-nucleated particles, such as the ultrasound contrast agent SonoVue® which has been widely used in clinical practice and MBs that match the ultrasound energy in the laboratory development stage. The micron vesicles have a diameter of 1-10 μm and can stably exist in the blood circulation. When irradiated by low-energy ultrasound, the gas nucleus of the MB undergoes resonance motion, and the local energy is amplified, resulting in a therapeutic effect. Although its therapeutic mechanism has not yet been completely clarified, in vivo and in vitro experiments have shown that LIFU+MB has a therapeutic effect of tumors comparable to that of high-intensity ultrasound. The use of MB reduces the intensity threshold of cell death caused by ultrasound alone and improves the therapeutic safety. A large amount of data also shows that LIFU+MB increases the efficacy of traditional chemotherapy drugs and radiotherapy. It can be seen that the efficacy and safety of LIFU+MB is positive, and it will be a new therapeutic technology with excellent prospects for clinical transformation, which brings hope for tumor patients, especially those who are refractory, resistant to traditional chemotherapy drugs, and unable to undergo traditional surgery.

SUMMARY

An objective of the present disclosure is to provide an ultrasound therapy system and a dose control method, which can be used to carry out LIFU-related and LIFU+MB-related cell experiments and animal experiments, or can also be used to carry out HIFU-related cell experiments and animal experiments. However, due to the use of a single ultrasound irradiation device in the prior art, it is difficult to carry out cell experiments and animal experiments. Especially in animal experiments, in order to fully observe the actual effect of ultrasound irradiation during the experiment, most of the animals need to be dissected. The same group of ultrasound irradiation doses may need to be repeatedly applied to the animals to be tested, and the actual effect of this group of ultrasound irradiation dose on the animals to be tested needs to be observed by dissection, which will result in a large number of animals to be dissected and complicated experimental operation process. It takes a long time to realize a complete experiment, and it is easy to introduce external factors that have an adverse effect on the whole experiment. In addition, it is difficult to determine the efficacy and safety of the ultrasound irradiation dose obtained in the cell experiment or animal experiment by carrying out only one of the cell experiment and animal experiment using the ultrasound irradiation device.

To achieve the above objective, the present disclosure provides an ultrasound therapy system, including:

a control device;

a first ultrasound irradiation device configured to generate multiple groups of ultrasound irradiation doses driven by the control device and conduct ultrasound irradiation on a cell culture device with multiple groups of abnormally proliferating living cells, where each group of ultrasound irradiation dose is applied to at least one group of abnormally proliferating living cells;

a characterization image capture device configured to capture performance characteristic data of living cells in the cell culture device, where the control device is further configured to determine an ultrasound irradiation dose corresponding to at least one group of abnormally proliferating living cells with a cell target characteristic characterization as a target ultrasound irradiation dose according to the performance characteristic data; and a second ultrasound irradiation device configured to conduct ultrasound irradiation of the target ultrasound irradiation dose on a living organism with abnormal proliferation.

Optionally, the ultrasound therapy system may further include:

an MB injection device configured to apply multiple groups of MB doses to the multiple groups of abnormally proliferating living cells prior to the ultrasound irradiation on the cell culture device with the multiple groups of abnormally proliferating living cells, where each group of MB dose may be applied to at least one group of abnormally proliferating living cells from a selected MB injection group of living cells in the cell culture device.

Optionally, the control device may further be configured to determine an MB dose corresponding to the at least one group of abnormally proliferating living cells with the cell target characteristic characterization as a target MB dose prior to the ultrasound irradiation of the target ultrasound irradiation dose on the living organism with abnormal proliferation.

The MB injection device may further be configured to apply the target MB dose to the living organism with abnormal proliferation prior to the ultrasound irradiation of the target ultrasound irradiation dose on the living organism with abnormal proliferation.

Optionally, the ultrasound therapy system may further include:

an MB injection device configured to apply a preset MB dose to the living organism with abnormal proliferation prior to the ultrasound irradiation of the target ultrasound irradiation dose on the living organism with abnormal proliferation.

Optionally, the control device may be provided with a parameter set configured to form any ultrasound irradiation dose.

The first ultrasound irradiation device may be configured to generate the multiple groups of ultrasound irradiation doses driven by the control device according to the parameter set, where any two groups of parameters in the parameter set may be different.

Optionally, the control device may further be configured to determine a group of parameters generating the target ultrasound irradiation dose as target parameters according to the target ultrasound irradiation dose.

The control device may further be configured to modify the target parameters to modified target parameters of the second ultrasound irradiation device.

The second ultrasound irradiation device may be configured to generate the target ultrasound irradiation dose driven by the control device according to the modified target parameters, and conduct ultrasound irradiation on the living organism with abnormal proliferation.

Optionally, the group of parameters each may include an ultrasound irradiation resonance frequency, an acoustic pressure, an acoustic intensity, a drive signal duty cycle, an MB dose, and an ultrasound irradiation time.

Optionally, the first ultrasound irradiation device and the second ultrasound irradiation device may each have a focused ultrasound transducer.

A maximum output ultrasound irradiation dose of the focused ultrasound transducer may be configured to be less than or equal to an upper dose limit. When the focused ultrasound transducer outputs the upper dose limit to egg white liquid or gel mixed with protein, the egg white liquid or the gel may just produce a biological focal region.

Optionally, a propagation coupling medium from the focused ultrasound transducer to the cell culture device in the first ultrasound irradiation device may be degassed water or a liquid coupling medium.

A propagation coupling medium from the focused ultrasound transducer to the living organism in the second ultrasound irradiation device may be degassed water, an acoustic coupling agent, or a liquid coupling medium.

Optionally, a focal region of the first ultrasound irradiation device may have a same or approximately same size as a focal region of the second ultrasound irradiation device.

Optionally, the control device may further be configured to determine that at least one of the performance characteristic data has a cell target characteristic characterization before the target ultrasound irradiation dose is determined according to the performance characteristic data. The cell target characteristic characterization may be a relative previous state or relative blank control group in the performance characteristic data, at least movement of living cells may be significantly slowed down in a current state, and the cells may be apoptotic immediately after a current group of ultrasound irradiation dose is applied or after the ultrasound irradiation is stopped.

Optionally, the control device may further be configured to determine that at least one of the performance characteristic data has a cell target characteristic characterization before the target ultrasound irradiation dose is determined according to the performance characteristic data. The cell target characteristic characterization may be a relative previous state or relative blank control group in the performance characteristic data, at least movement of living cells may be significantly slowed down in a current state, and the cells may remain viable within a predetermined time range after a current group of ultrasound irradiation dose is applied or after the ultrasound irradiation is stopped.

The example of the present disclosure provides an ultrasound irradiation device, including: a signal source, a water tank, a focused ultrasound transducer, and a support frame.

The focused ultrasound transducer is connected to the signal source and is arranged and embedded at a bottom of the water tank.

The support frame is arranged at a bottom position of the water tank corresponding to the focused ultrasound transducer.

The water tank is filled with a liquid coupling medium matching a height of the support frame.

The support frame is provided with the aforementioned cell culture device.

The example of the present disclosure provides an ultrasound irradiation device, including: a signal source, a focused ultrasound transducer, and a housing.

The focused ultrasound transducer is connected to the signal source.

An installation cavity is arranged inside the housing.

The focused ultrasound transducer is provided with a probe and a water bag connected to the probe, and the water bag is filled with degassed water or a liquid coupling medium.

The probe and the water bag are arranged in the installation cavity.

The focused ultrasound transducer conducts ultrasound irradiation on the aforementioned living organism through the water bag.

The example of the present disclosure provides a dose control method, including:

driving a first ultrasound irradiation device to generate multiple groups of ultrasound irradiation doses, and conducting ultrasound irradiation on a cell culture device with multiple groups of abnormally proliferating living cells, where each group of ultrasound irradiation dose is applied to at least one group of abnormally proliferating living cells;

obtaining characteristic characterization data of living cells in the cell culture device;

determining an ultrasound irradiation dose corresponding to at least one group of abnormally proliferating living cells with a cell target characteristic characterization as a target ultrasound irradiation dose according to the characteristic characterization data; and driving a second ultrasound irradiation device to conduct ultrasound irradiation of the target ultrasound irradiation dose on a living organism with abnormal proliferation.

Corresponding to the above content, the concept of the present disclosure supports the use in different intensity focused ultrasound therapy systems, especially for LIFU therapy systems. The present disclosure realizes the dose control of a self-defined object in the abnormal proliferation inhibition treatment process or in the experimental process, and the self-defined object may be a certain cell of a self-defined abnormal proliferation type or a certain abnormally proliferating self-defined living organism type. Under the determined device and connection structure, the influence parameter of the dose can have a single dimension, for example, the time when the control device drives the first ultrasound irradiation device to irradiate. Both of the first ultrasound irradiation device and the second ultrasound irradiation device can be uncalibrated. The first ultrasound irradiation device can be calibrated with relative doses by the multiple groups of living cells. The second ultrasound irradiation device supports formation of the target ultrasound irradiation dose through the switching behavior or is controlled by the control device together to form the target ultrasound irradiation dose (can be only a single-dimensional parameter, such as time). The characteristic characterization data of each group of living cells (such as time growth rate) reflects the relative ultrasound irradiation dose, and the dose applied to the corresponding group of living cells (for example, the application time) can be selected as the target ultrasound irradiation dose.

The ultrasound therapy system further introduces the MBs to participate in ultrasound irradiation, which can also determine the target MB dose that is effective for abnormally proliferating subjects and harmless with respect to shift and scattering adjacent tissues.

The ultrasound therapy system introduces multi-dimensional parameters, which can relatively quantize the ultrasound irradiation dose through the control device (such as a timing signal). The relative value of ultrasound irradiation of the multiple groups of living cells can be taken as the target parameter without using acoustic detection devices such as hydrophones (for example, one group is used as a reference, and the doses of other groups are expressed through timing signals).

The ultrasound therapy system determines the upper dose limit of the focused ultrasound transducer through egg white liquid or gel mixed with protein (such as hydrogel mixed with protein), such that each ultrasound irradiation device of the ultrasound therapy system is in the LIFU range.

By using the same propagation coupling medium, the ultrasound therapy system can reduce the incremental change of the corrected target parameter relative to the target parameter, that is, it can be used for the second ultrasound irradiation device without excessively correcting the target parameter.

The size of the focal region of the second ultrasound irradiation device of the ultrasound therapy system is preferably the same as that of the focal region of the first ultrasound irradiation device, such that the dose in the first ultrasound irradiation device can be directly used or slightly modified for the second ultrasound irradiation device. The second ultrasound irradiation device conducts ultrasound irradiation on a local part of the living organism, and the second ultrasound irradiation device can preferably be a hand-held and portable focused ultrasound irradiation device.

The ultrasound therapy system can be as close as possible to the maximum safe ultrasound irradiation dose. By characterizing the characteristics of each group of cells, the dose corresponding to a group of cells that die or are apoptotic immediately after the ultrasound irradiation is stopped is taken, so as to obtain a sufficient and effective upper dose limit.

In the present disclosure, within the safe range of ultrasound irradiation dose, the dose corresponding to a group of cells with significantly slowed-down movement of living cells that are viable after the ultrasound irradiation is stopped is taken, and can achieve abnormal proliferation inhibition, which is a preferred effective dose. The present disclosure can quickly determine the target dose of a therapy system that has never been calibrated and has an ultrasound irradiation device. The target dose is effective for abnormally proliferating subjects and harmless with respect to focal region shift and acoustic scattering adjacent tissues, such as disorganized hemorrhage.

Other features and advantages of examples of the present disclosure are described in detail in the subsequent specific implementation part.

BRIEF DESCRIPTION OF THE DRAWINGS

The accompanying drawings are provided for further understanding of the examples of the present disclosure, and constitute a part of the specification. The accompanying drawings and the following specific implementations are intended to explain examples of the present disclosure, rather than to limit the examples of the present disclosure. In the figures.

TERMS IN THE DRAWINGS

Figure 1:
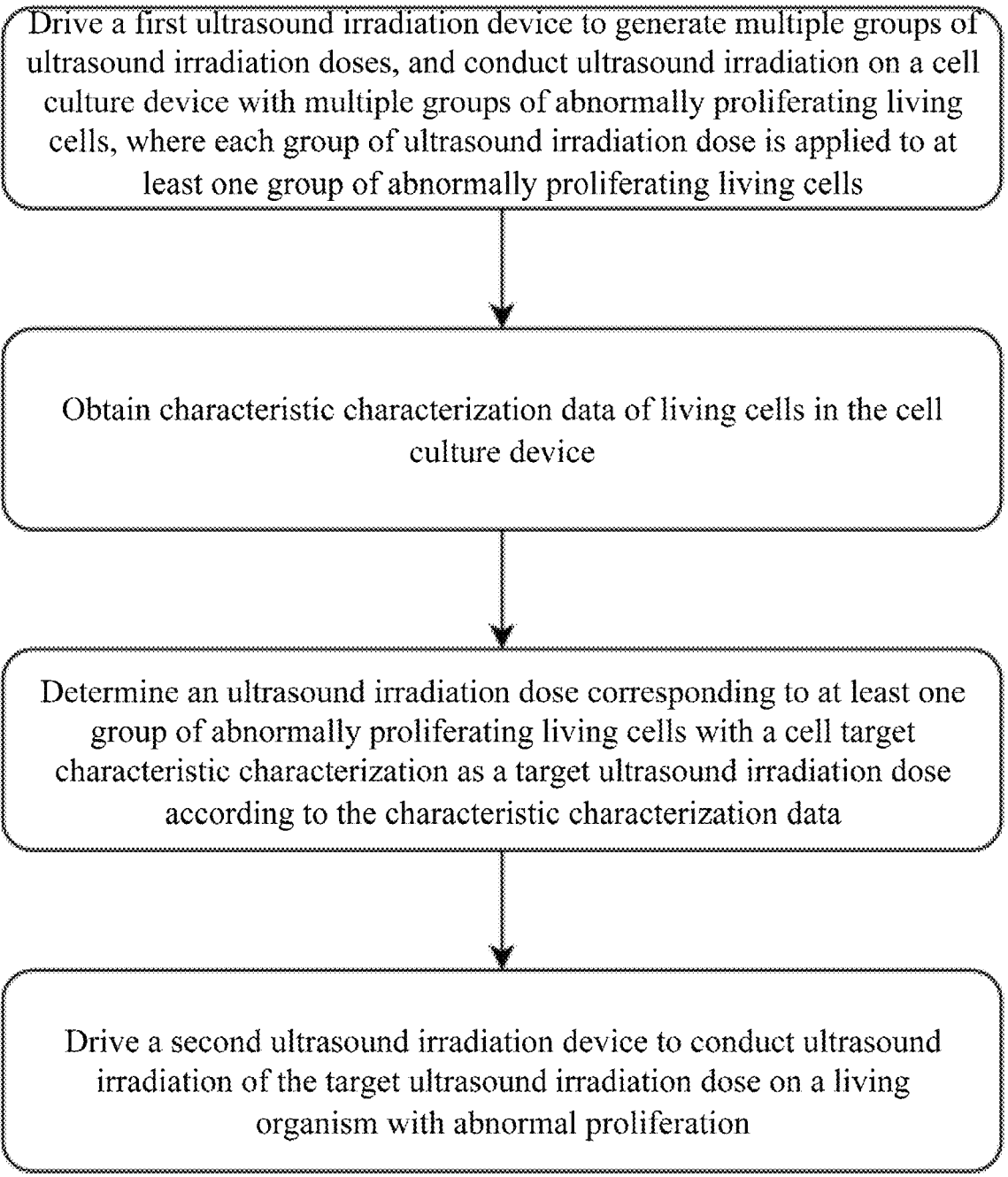
FIG. 1 is a schematic flowchart of a main method of dose control according to an example of the present disclosure.

Optical Density (OD) refers to an optical density. Control, Con, C, and con-P1 are blank control groups. MB is an MB group. LIFU is a cell group irradiated by LIFU. LIFU+MB is a cell group irradiated by LIFU combined with MBs. Invasion refers to invasion. Migration refers to migration. Propidium Iodide (PI) is propidium iodide (staining). FITC and PE-CF594 are fluorescein. Relative migration rate refers to a relative migration rate. Number of cell refers to a number of cells. Beclin 1 is protein (encoded by a BECN1 gene). p62 is protein. GAPDH is protein. anti-GAPDH is an antibody (as an internal reference for western blot and quantitative reverse transcriptase polymerase chain reaction (qRT-PCR)). LC3B (I and II) is protein. Relative mRNA expression is relative expression of single-stranded DNA molecules. Treatment is a cell group irradiated by LIFU combined with MBs. DAPI is a nuclear dye. GFP is green fluorescent protein. mCherry is red fluorescent protein. Merge is a combination of different fluorescence filters. autophagosomes refer to autophagosomes. autolysosomes refer to autolysosomes. Paclitaxel refers to paclitaxel. The volume of tumor refers to the volume of tumor. H&E refers to hematoxylin and eosin staining. LC3B intensity (fold) represents a staining intensity of LC3B protein. Cum survival is a cumulative survival time. UL, UR, LR, and LL, and Q1, Q2, Q3, and Q4 are quadrant marks.

DETAILED DESCRIPTION OF THE EMBODIMENTS

Specific implementations of the examples of the present disclosure are described in detail below with reference to the accompanying drawings. It should be understood that the implementations described herein are merely intended to illustrate and interpret the examples of the present disclosure, rather than to limit the examples of the present disclosure.

Example 1

The example of the present disclosure provides an ultrasound therapy system, including: a control device, a first ultrasound irradiation device, a characterization image capture device, and a second ultrasound irradiation device.

The control device is included.

The first ultrasound irradiation device is configured to generate multiple groups of ultrasound irradiation doses driven by the control device and conduct ultrasound irradiation on a cell culture device with multiple groups of abnormally proliferating living cells. Each group of ultrasound irradiation dose is applied to at least one group of abnormally proliferating living cells.

The characterization image capture device is configured to capture performance characteristic data of living cells in the cell culture device.

The control device is further configured to determine an ultrasound irradiation dose corresponding to at least one group of abnormally proliferating living cells with a cell target characteristic characterization as a target ultrasound irradiation dose according to the performance characteristic data.

The second ultrasound irradiation device is configured to conduct ultrasound irradiation of the target ultrasound irradiation dose on a living organism with abnormal proliferation.

Abnormal proliferation of abnormally proliferating living cells, or abnormal proliferation of living organisms with abnormal proliferation, could be caused by the presence of cancer cells. The source of abnormally proliferating living cells, such as at least a certain number of viable cancer cells (such as pre-cultured cell lines), could be human beings or other animals, such as nude mice. The ultrasound therapy system could further include: a blank control group that met specific experimental purposes, and the blank control group could have multiple groups of living cells. For the living cells or abnormally proliferating living cells in the blank control group, for different specific experiments, a variety of methods for observing and recording the cell state could be used. Any living cell could be a real living cell or a cell sample with living cell status recorded after cell preparation, depending on the stage of the specific experiment combined with the observation method. A cell culture device could be a cell culture dish. In cell target characteristic characterization, for example, performance characteristic data of cells, the movement of cells, such as migration or invasion, was significantly slowed down. The characteristics of chemoresistant cells, such as increased sensitivity to drugs, could be used as the cell target characteristic characterization. The living organism could be an animal with life characteristics, such as a live nude mouse. Optionally, the living organism with abnormal proliferation could be a living organism with a cancer cell, which could be a human cell transplant, a cancer cell transplant from an animal of the same type as the living organism, or a cancer cell transplant from an animal with a different type of living organism. That is, the abnormal proliferation of living organisms and the abnormal proliferation of cells could be of the same type or of different types. Herein, the living organism (for example, at least two nude mice) was the subject to be tested, and there could be more than one living organisms. The type could be changed to a certain animal type according to the specific experiment.

In some specific implementations, the control device could optionally include a computer that provided additional functions such as data processing, data recording, signal control, and device driving, and was optionally provided with display equipment having a function of presenting characterization data of living organism characteristics and cell characteristics of a characterization image capture device. Optionally, the control device could also be a server provided with a pre-trained neural network detection model and an object tracking model in order to provide an automatic function, which could recognize, track and count the survival or apoptosis of living cells in the cell culture device, record the survival status over time and record the number of cells.

In some specific implementations, preferably, the control device only had or could also include one or more configurable signal generators. The first ultrasound irradiation device and the second ultrasound irradiation device were driven by the one or more signal generators. Optionally, each ultrasound irradiation device could have an independent controller.

Optionally, one or more signal generators each drove the first ultrasound irradiation device and the second ultrasound irradiation device through auxiliary circuits, such as amplifier circuits and filter circuits.

In some specific implementations, each ultrasound irradiation device, preferably, could only include an ultrasound probe and a mechanical structure for auxiliary purposes such as fixing and packaging of the ultrasound probe. The controller and auxiliary driving circuit configured to drive the ultrasound probe could be regarded as a part of the control device.

In some specific implementations, the characterization image capture device could be configured to capture performance characteristic data of cells in the cell culture device and performance characteristic data of the state of tissues and organs in the living organism. At this time, the characterization image capture device could be configured to obtain performance characteristic data of the living organism irradiated by the second ultrasound irradiation device. The characterization image capture device could be a microscope (e.g., a scanning electron microscope), a camera and/or other devices with charge-coupled devices, could have a processor, or could simply transmit captured performance characteristic data to the control device to provide necessary cell image data acquisition.

In some specific implementations, considering specific experimental needs, the performance characteristic data could be image data. Further, data processing could be conducted on the performance characteristic data combined with the preset processing rules. Different data processing procedures and types could be selected for the data processing according to the specific experimental purpose. For example, the captured performance characteristic data could be statistically processed through the preset processing rules, and the processed performance characteristic data could also be image data, but at this time, specific parts of cells or animal organs on the image data could be marked and enhanced, and the statistical number of cells could be presented. Further, data classification could also be conducted on the performance characteristic data combined with the classification mapping rules. According to the specific experimental purpose, after the data classification operation, text data of specific classification could be obtained, such as whether there was a significant decrease in scratch repair ability or migration ability of cells, whether there was a large number of cell death or apoptosis, whether there was a significant change in the expression level of specific proteins (such as autophagy levels), and whether there was a significant increase in drug permeability. The aforementioned text data or image data could be used as the final performance characteristic data output by the characterization image capture device according to the captured performance characteristic data.

On the basis of the aforementioned content, the performance characteristic data with the cell target characteristic characterization was selected from the performance characteristic data. According to the corresponding relationship, an ultrasound irradiation dose corresponding to at least one group of abnormally proliferating living cells with the cell target characteristic characterization could be found. The cell target characteristic characterization could be the aforementioned content that there was a significant decrease in scratch repair ability or migration ability of cells, there was a large number of cell death or apoptosis, there was a significant increase in permeability of a large number of cells to specific drugs, and there was a significant change in the expression level of specific proteins.

In some specific implementations, both the first ultrasound irradiation device and the second ultrasound irradiation device could be a water tank-type ultrasound irradiation device or a hand-held ultrasound irradiation device, but preferably, the first ultrasound irradiation device was a water tank-type ultrasound irradiation device, which could be used to conduct cell experiments, and the second ultrasound irradiation device was a hand-held ultrasound irradiation device, which could be used to conduct animal experiments.

In some specific implementations, for example, in cell experiments or animal experiments, LIFU irradiation was conducted on cells or animals injected with MBs, and the MB injection device could be a syringe such as an injection syringe or an MB injection gun. Optionally, for cell experiments and animal experiments, the target MB dose in animal experiments could be derived from cell experiments. Optionally, a preset MB dose could be used in animal experiments, for example, an MB dose of 100 ul was applied to each mouse, and the preset MB dose could be selected and determined through multiple groups of control experiments.

In some specific implementations, the first ultrasound irradiation device and the second ultrasound irradiation device each had a focused ultrasound transducer.

A maximum output ultrasound irradiation dose of the focused ultrasound transducer was configured to be less than or equal to an upper dose limit. When the focused ultrasound transducer output the upper dose limit to egg white liquid or gel, the egg white liquid or the gel just produced a biological focal region.

In addition, the upper limits of the first ultrasound irradiation device and the second ultrasound irradiation device were determined through the egg white liquid or the gel.

In some specific implementations, the control device was further configured to determine that at least one of the performance characteristic data had a cell target characteristic characterization before the target ultrasound irradiation dose was determined according to the performance characteristic data. The cell target characteristic characterization was a relative previous state or relative blank control group in the performance characteristic data, at least movement of living cells was significantly slowed down in a current state, and the cells were apoptotic immediately after a current group of ultrasound irradiation dose was applied or after the ultrasound irradiation was stopped.

At this time, the previous state and the current state could be relative to the acquisition cycle of the cell characteristic characterization data, such as the previous acquisition cycle. The previous state and the current state could also be relative to the experimental time. For example, the experimental time was divided into multiple time periods. The cell group used as a reference in the previous state could be the cell group that had not been given any dose, or the cell group that had been given some doses. The cell group could be one of the aforementioned multiple groups of abnormally proliferating living cells, and the cell group could also be a blank control group that met the experimental purpose. The performance characteristic data in the current time period was data with cell target characteristic characterization and cell survival characteristics in the current state. The performance characteristic data in the previous time period was data with cell target characteristic characterization and cell survival characteristics in the previous state.

Whether there were cell target characteristics in the performance characteristic data was determined, and if so, the cell target characteristics were determined.

Relative to the aforementioned upper limit, here, the secondary upper limit could be further determined. For example, if the ultrasound irradiation dose corresponding to the upper limit and the ultrasound irradiation dose corresponding to the secondary upper limit had a one-dimensional parameter of ultrasound irradiation time, the ultrasound irradiation time corresponding to the upper limit was greater than the ultrasound irradiation time corresponding to the secondary upper limit. If the ultrasound irradiation dose corresponding to the upper limit and the ultrasound irradiation dose corresponding to the secondary upper limit were both regarded as power per unit area in the focal region, the power per unit area in the focal region corresponding to the upper limit was greater than the power per unit area in the focal region corresponding to the secondary upper limit.

When any ultrasound irradiation device used the second upper limit, the focused ultrasound transducer of any ultrasound irradiation device was configured to output the ultrasound irradiation dose corresponding to the secondary upper limit. When the focused ultrasound transducer output the secondary upper limit to the living cells, the living cells received the ultrasound irradiation dose of the secondary upper limit. The cells were death or apoptotic immediately after the ultrasound irradiation was applied or after the ultrasound irradiation was stopped.

In some specific implementations, the control device was further configured to determine that at least one of the performance characteristic data had a cell target characteristic characterization before the target ultrasound irradiation dose was determined according to the performance characteristic data. The cell target characteristic characterization was a relative previous state or relative blank control group in the performance characteristic data, at least movement of living cells was significantly slowed down in a current state, and the cells remained viable within a predetermined time range after a current group of ultrasound irradiation dose was applied or after the ultrasound irradiation was stopped. Through the operation, the obtained ultrasound irradiation dose was a preferred value, which was effective and was harmless with respect to focal region shift and acoustic scattering adjacent tissues.

The predetermined time range could eliminate the hysteresis of the effect of ultrasound irradiation on cells, and the specific value could be selected through the normal life cycle of living cells or a pre-defined value could be taken, such as 24 h.

When any ultrasound irradiation device used the preferred value, the focused ultrasound transducer of any ultrasound irradiation device was configured to output an ultrasound irradiation dose corresponding to the preferred value. When the focused ultrasound transducer output the preferred value to the living cells, at least movement of the living cells was significantly slowed down when subjected to the ultrasound irradiation dose of the preferred value, and the cells remained viable within a predetermined time range after the ultrasound irradiation was applied or after the ultrasound irradiation was stopped.

In some specific implementations, the specific value of the parameter could be mapped to the specific value of the ultrasound irradiation dose by assigning a weight ratio or a weight coefficient.

Example 2

Figure 10:
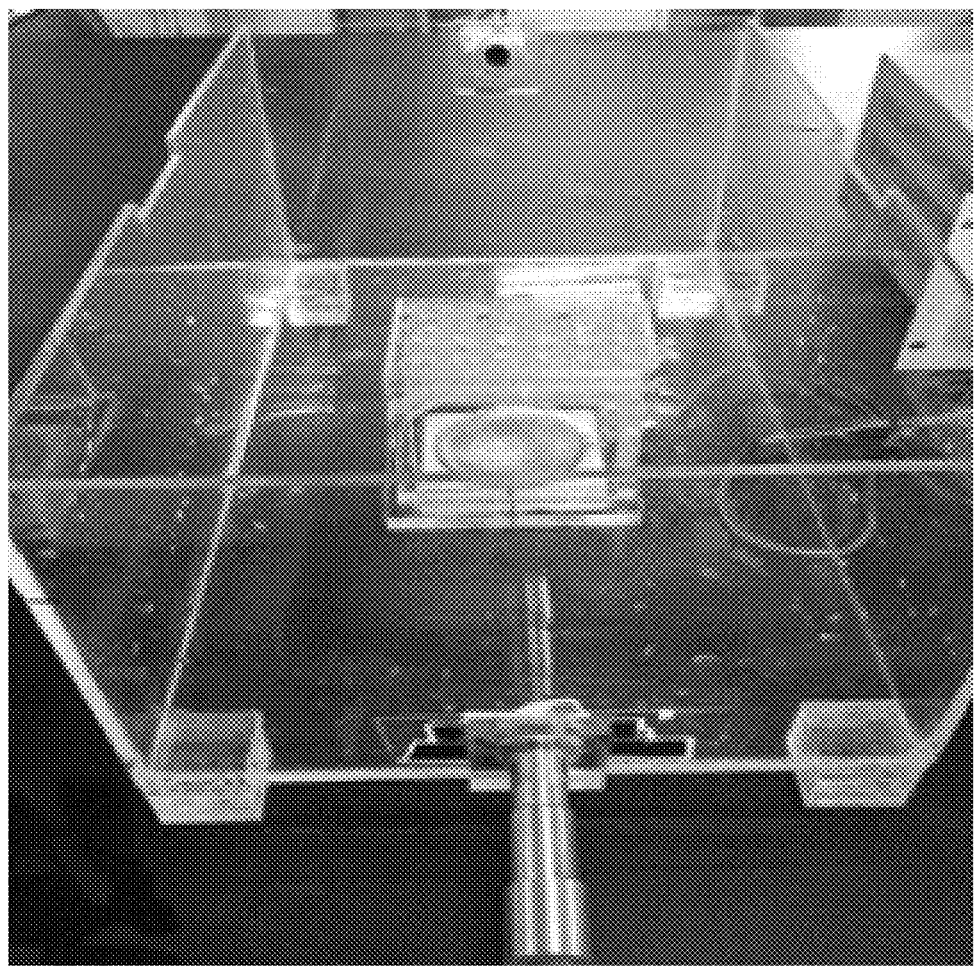
FIG. 10 is a physical schematic diagram of an exemplary water tank-type ultrasound irradiation device according to the example of the present disclosure.

As shown in FIG. 10 (a coupling medium such as degassed water is hidden in the figure), the example of the present disclosure provides an ultrasound irradiation device, which can be used as the first ultrasound irradiation device in Example 1. The ultrasound irradiation device includes: a signal source, a water tank, a focused ultrasound transducer, and a support frame.

The focused ultrasound transducer is connected to the signal source and is arranged and embedded at a bottom of the water tank.

The support frame is arranged at a bottom position of the water tank corresponding to the focused ultrasound transducer.

The water tank is filled with a coupling medium, such as degassed water or a liquid coupling medium, matching a height of the support frame.

The support frame is provided with the aforementioned cell culture device.

The signal source can be driven or configured by the aforementioned control device.

Example 3

Figure 11:
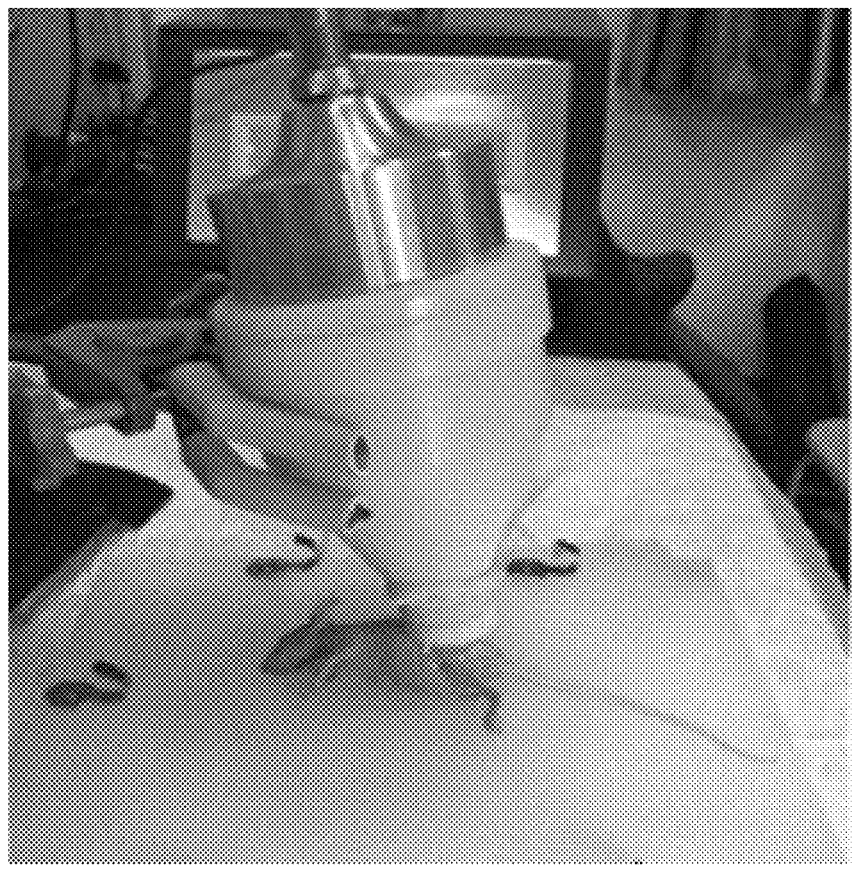
FIG. 11 is a physical schematic diagram of an exemplary hand-held ultrasound irradiation device according to the example of the present disclosure.

As shown in FIG. 11, the example of the present disclosure provides an ultrasound irradiation device, which can be used as the second ultrasound irradiation device in Example 1. The ultrasound irradiation device includes: a signal source, a focused ultrasound transducer, and a housing.

The focused ultrasound transducer is connected to the signal source.

The housing includes a probe installation cavity and a water bag installation cavity. The housing further includes an ultrasound outlet area. The probe installation cavity, the water bag installation cavity, and the ultrasound outlet area are arranged in the housing in sequence.

The focused ultrasound transducer is provided with a probe and a water bag connected to the probe. The water bag is filled with degassed water. The degassed water is used as (propagation) a liquid coupling medium for ultrasound (from the position of the probe to the ultrasound outlet area) emitted by the focused ultrasound transducer.

The probe is arranged in the probe installation cavity, and the water bag is arranged in the water bag installation cavity.

The focused ultrasound transducer conducts ultrasound irradiation on the aforementioned living organism through the water bag.

Optionally, a fixing clip is installed outside the housing, and the fixing clip is provided with a hand-held rod. The signal source can be driven or configured by the aforementioned control device.

There is no need to re-configure the parameters of the focused ultrasound transducer at this time, and the parameters of the focused ultrasound transducer in Example 2 can be directly used or slightly modified.

Example 4

Based on Examples 1 to 3, different equipment structures and parameter combinations caused significant differences in the acoustic field. It was difficult to find a group of equipment structures and equipment operating parameters that could emit irradiation with inhibitory effects and could not kill normal tissue cells. It was very likely that the optimal parameter combination had not been found while the cells had already been apoptotic (apoptosis was caused by irradiation on the one hand, and on the other hand, the survival time of tumor cells was limited, and the living organism could not provide a lot of test time).

Especially for the treatment process or experimental process of the combination of LIFU irradiation and MBs, it was very likely that the optimal effect could not be observed all the time if the parameters or structure were adjusted for MBs or cell states alone (either for the safety of tissue cells, the irradiation dose was too small, or the irradiation was too strong, causing certain damage), or it was impossible to know whether the current MBs or cells were in an acceptable course of treatment. The example of the present disclosure provided dose control for the LIFU+MB treatment process. The dose control was closely related to the cell state and MB properties of the cancerous organisms, such that a group of devices and parameters for devices of a therapeutic device that emitted irradiation with inhibitory effects for cancerous organisms and did not damage normal tissue cells of the organism could be found.

For MBs, ultrasound cavitation referred to the dynamic process of contraction, expansion and collapse when the acoustic pressure reached a certain value when the micro-gas nucleus cavitation bubbles in the liquid vibrated under the action of acoustic waves. According to the effect of different intensities of acoustic waves and the changes of MBs, it was divided into two forms: stable cavitation and inertial cavitation. Stable cavitation referred to stable oscillation of gas-nucleated MBs along the resonance diameter under the excitation of low-energy (generally considered less than 1.4 MPa) acoustic waves. It was manifested as the alternating movement of MB volume contraction and expansion, which pushed and pulled the surrounding blood vessel wall, resulting in the increase of the space between vascular epithelial cells, or squeezed and stretched the cell membrane, resulting in changes in the arrangement of the cell membrane and the formation of temporary pores. Inertial cavitation referred to a process that under higher ultrasound intensity (generally considered greater than 1.4 MPa), the MBs experienced more severe expansion, contraction and strong collapse, or stable cavitation continuously gathered the energy of the acoustic field, and when the energy reached a certain threshold, the cavitation bubble collapsed sharply. The cavitation bubble had a service life of about 0.1 μs, could release huge energy when collapsed sharply, and generated a micro jet with a speed of about 110 m/s and a strong impact force, making the collision density as high as 1.5 kg/cm$^2$. The cavitation bubbles generated local high temperature and high pressure (5,000 K, 1,800 atm) at the moment of sharp collapse. Inertial cavitation created a greater impact on surrounding tissues and cells, or led to the formation of irreversible pores on biological barriers such as blood vessels and cell membranes, thereby increasing drug permeability. The huge impact and thermal effects generated by higher ultrasound energy could directly cause cell death.

Sonoporation, also known as cell sonoporation, used acoustic waves to change the permeability of cell membranes. This technique was commonly used in molecular biology and non-viral gene therapy to allow macromolecules such as DNA to enter cells, so as to increase the transfection or transformation of drugs, and cause cell death. Acoustic waves enhanced the transport of these macromolecules through the cavitation of the MBs. The biological activity of this technique was similar to, and in some cases even superior to, electroporation.

At present, in the process of introducing foreign genes into tissue culture cells, especially mammalian cells, using the combined technology of acoustic waves and MBs was in the active stage of research and had shown excellent results, which solved the problem that the emerging gene therapy was difficult to be recognized by cells and transfected in cells. The combined technology of ultrasound combined with MB had also been applied to the study of drug sensitization of traditional therapy methods (such as chemotherapy drugs). Through the effect of sonoporation, the endocytosis of drugs could be increased, and the effectiveness of drugs could be improved by 20-80%. The drug modified by the acoustic-sensitive material was not released in the area not irradiated by the acoustic wave, which reduced the accumulation of the drug in the normal organs and reduced the toxic and side effects of the chemotherapy drugs.

In the complex tumor microenvironment, the drug sensitization effect induced by ultrasound was not a single mechanism, but also a complex process. There were sonoporation effects caused by the cavitation effect of MBs at three levels of blood vessels, spaces, and cells. The core content was that MBs and anti-tumor drugs (drug-loaded MB community or MB drug mixture) stably existed in the blood circulation system after intravenous injection. The sonoporation effect synergistically produced by the ultrasound MBs broke the biological barrier of the tumor blood vessel wall, and more drugs diffused into the tissue space of tumor cells through the vascular endothelial space. Then, under the irradiation force of the acoustic waves, the drug overcame the high pressure in the interstitial space and was pushed to a distance far away from the blood vessel. At this time, the concentration of the drug in the interstitial space increased, and the distribution range increased. Then, in the process of drug cross-cell membrane, the ultrasound broke the biological barrier of cell membrane through sonoporation on the cell surface, so as to promote ingestion of more drugs by cells, exerting drug effect, and finally leading to the death of tumor cells in a targeted manner.

The ultrasound irradiation devices in the examples of the present disclosure could be composed of an arbitrary waveform transmitter, a power amplifier, and a focused ultrasound probe (focused ultrasound transducer), and could also be provided with a programmable controller. The controller was connected to the arbitrary waveform transmitter to form a signal source, which had the characteristics of acoustic energy focusing and multi-parameter continuous adjustment, and realized accurate control of the irradiation target area and energy. The signal emitted by the signal source was amplified by the power amplifier and loaded into the focused transducer as an excitation signal. By adjusting the parameters of the signal source and the power amplifier, the acoustic intensity in the focal region could be accurately adjusted.

The examples of the present disclosure used the structures of the aforementioned ultrasound irradiation devices, which were a water tank-type low-intensity ultrasound irradiation device and a hand-held low-intensity ultrasound irradiation device. The former was suitable for cytological experiments first, and the latter could be used to conduct appropriate animal experiments based on the former.

For the calibration of the focusing characteristic acoustic field and focusing characteristic of the probe in the ultrasound irradiation device, the parameters of the radiated acoustic field (radiated acoustic power, acoustic pressure, etc.) of the transducer were measured many times, and the results showed that the characteristics were stable. First, through simulation model calculation and simulation test verification, the acoustic field distribution was checked, and then the hydrophone was used to measure and calibrate the acoustic characteristics of the focal region, as follows:

(1) The measured values of the acoustic field (fundamental wave and second and third harmonics) of the water tank-type focused transducer were compared with the simulated values, and the results were relatively consistent, with characteristics such as stable acoustic wave generation and energy distribution.

(2) The hydrophone of the probe measured the acoustic pressure information at the focal region of the focused transducer.

The hydrophone calibrated acoustic pressure characteristics of the probe: the hydrophone of the probe was used for calibration. The hydrophone was placed at the place with the strongest acoustic pressure during measurement. The data was read by an oscilloscope for calculation. For example: the amplitude of the arbitrary waveform transmitter of the signal was adjusted. When the peak-to-peak value displayed by the oscilloscope was 860 mVpp, the corresponding acoustic pressure was 0.21 MPa, from which Table 1 could be obtained.

TABLE 1

Calibration parameters of acoustic pressure of water tank-type probe

| Acoustic pressure (Mpa) | Acoustic intensity (W/cm$^2$) | Hydrophone (mVpp) | Signal source (mVpp) | Duty cycle (%) | Temperature (° C.) | |
|---|---|---|---|---|---|---|
| 0.12 | 1 | 831 | 480 | 20 | 37 | Output selection gear: 70 V 2.8A 25Ω |
| 0.17 | 2 | 1176 | 690 | 20 | 38 | |
| 0.21 | 3 | 1400 | 860 | 20 | 38.8 | |
| 0.24 | 4 | 1663 | 1000 | 20 | 39.6 | |
| 0.27 | 5 | 1859 | 1169 | 20 | 40.5 | |

The signal source took 5% duty cycle: number of cycles=590; 10% duty cycle: number of cycles=1,180; 15% duty cycle: number of cycles=1,770; and 20% duty cycle: number of cycles=2,360. For acoustic pressure calibration of the hand-held probe, signal source correction was conducted, and Table 2 could be obtained.

TABLE 2

Calibration parameters of acoustic pressure of hand-held probe

| Acoustic pressure (Mpa) | Acoustic intensity (W/cm$^2$) | Hydrophone (mVpp) | Signal source (mVpp) | Duty cycle (%) | Temperature (° C.) |
|---|---|---|---|---|---|
| 0.12 | 1 | 831 | 390 | 20 | 37 |
| 0.17 | 2 | 1176 | 610 | 20 | 38 |
| 0.21 | 3 | 1400 | 800 | 20 | 38.8 |

(3) The egg white in vitro model experiment was conducted to detect the focusing performance.

It was shown that the medium-energy ultrasound caused the protein to coagulate into small granular nodules, while the egg white in the non-focal region did not coagulate, which intuitively showed the excellent focusing characteristics of the equipment. The egg white experiment showed that the medium-intensity ultrasound irradiation was conducted for 3 min under an acoustic pressure of 0.35 MPa, an acoustic intensity of 7 W/cm$^2$, and 100% duty cycle, the protein in the focal region coagulated and denatured (just generating the biological focal region), and the protein in the non-focal region did not coagulate, showing the excellent focusing characteristics of the equipment.

(4) Calibration of tumor cell apoptosis and proliferation was conducted.

In the previous study of cell culture device, cell counting kit-8 (CCK-8) assay was used to detect the inhibition of LIFU+MB on the proliferation of ovarian cancer cells SKOV3 and HO8910PM. The results showed that the proliferation of both cell lines was significantly inhibited and the apoptosis rate was significantly increased. It should be noted that FIG. 2 to FIG. 9 combine several parts of experimental data (image or statistical data) control subgraphs, which makes it easier to understand the experimental data and check the experimental effect. For example, FIG. 5 has four parts of A, B, C, and D, FIG. 6 has eleven parts of A, B, C, D, E, F, G, H, I, J, and K, and FIG. 7 has six parts of A, B, C, D, E, and F.

Figure 2:
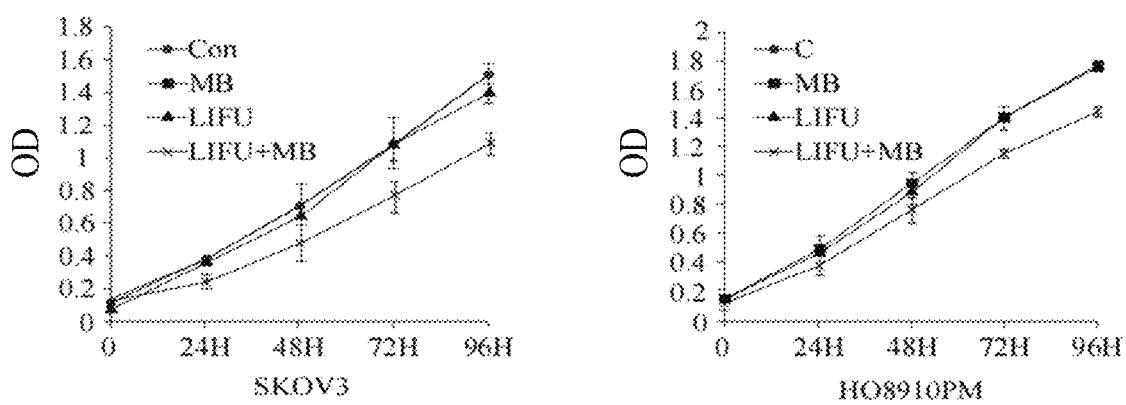
FIG. 2 is a schematic diagram of time growth curves of optical densities of cells with different treatments according to the example of the present disclosure.

As shown in FIG. 2, CCK8 detects time growth curves of SKOV3 and HO8910PM cells in the blank control group, the MB group, the LIFU group, and the LIFU+MB group after treatment for 72 h. The cells in both groups show cell proliferation inhibition in the LIFU+MB group with optimal energy, but this phenomenon does not occur immediately after irradiation, but a hysteresis effect after irradiation. There is no significant difference in the proliferation inhibition among the cells in the other three groups.

Figure 4:
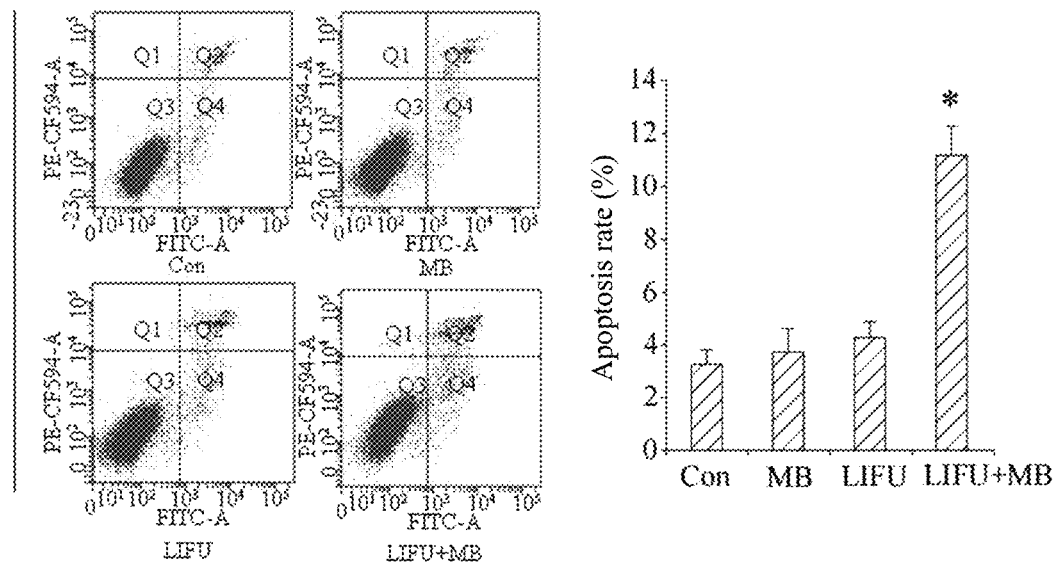
FIG. 4 is a schematic diagram of apoptosis of cells after different treatments for 24 h according to the example of the present disclosure.
Figure 4:
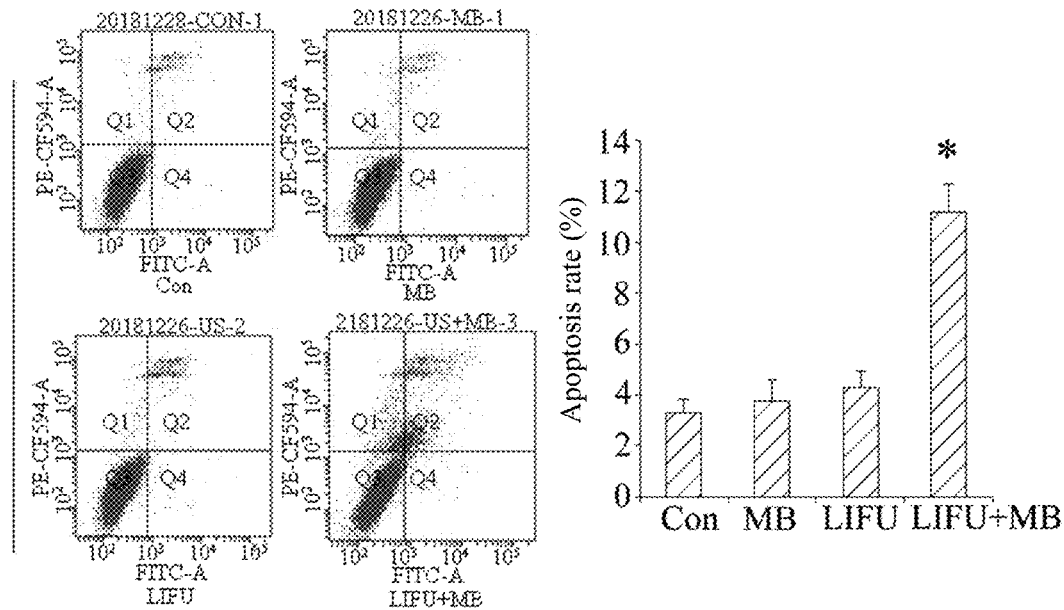

As shown in FIG. 4, apoptosis rates of SKOV3 and HO-8910PM cells in the blank control group, the MB group, the LIFU group, and the LIFU+MB group after treatment for 24 h are detected by flow cytometry. The cells in both groups show a significant increase in apoptosis rate in the LIFU+MB group with optimal energy. There is no significant difference in the apoptosis among the cells in the other three groups. * indicates that the difference is statistically significant. At this time, the applied ultrasound irradiation dose can be used as the secondary upper limit in Example 1, or a control experiment can be conducted here using the secondary upper limit obtained in Example 1.

Figure 3:
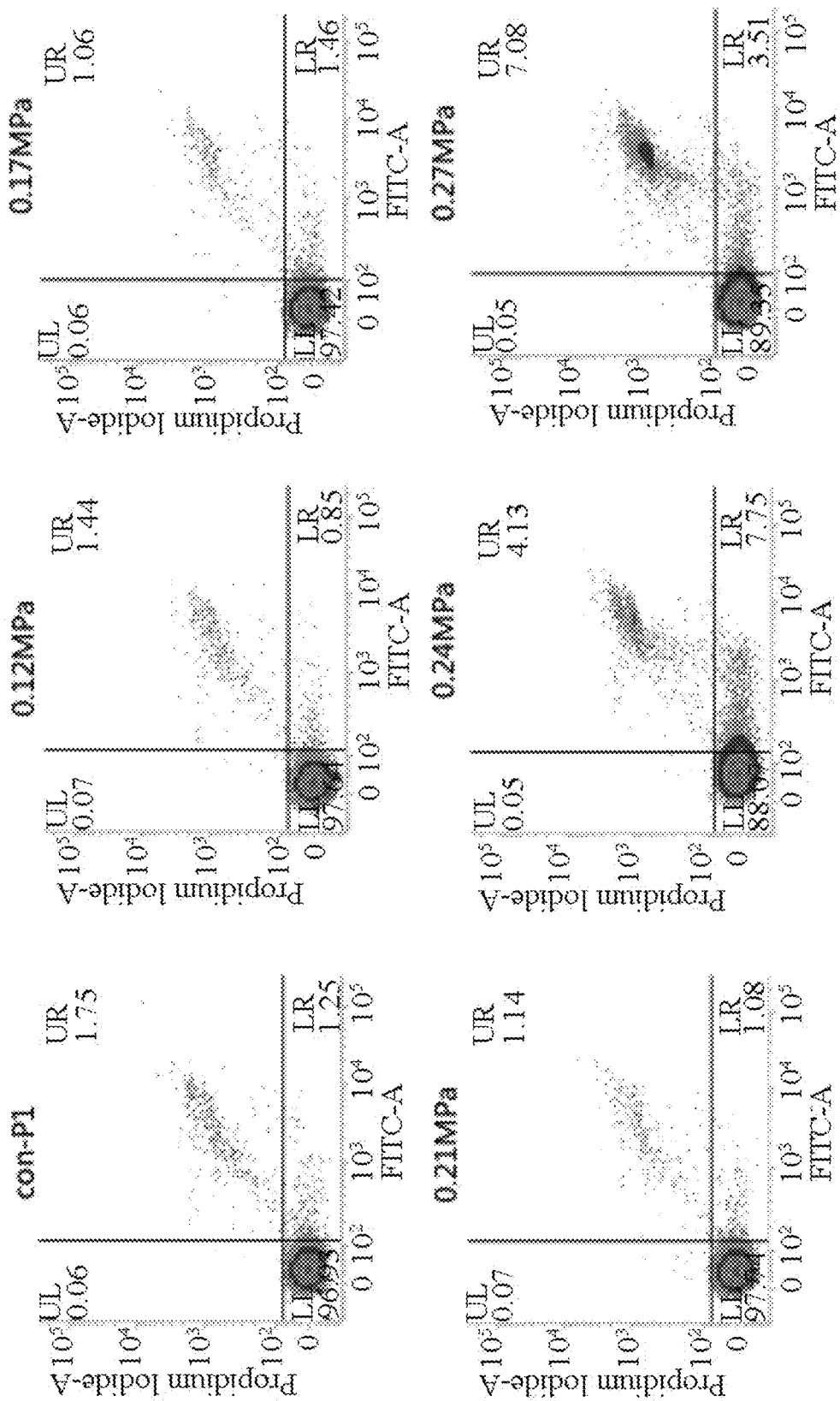
FIG. 3 is a schematic diagram of instantaneous apoptosis of cells after irradiation of different ultrasound doses according to the example of the present disclosure.
Figure 7:
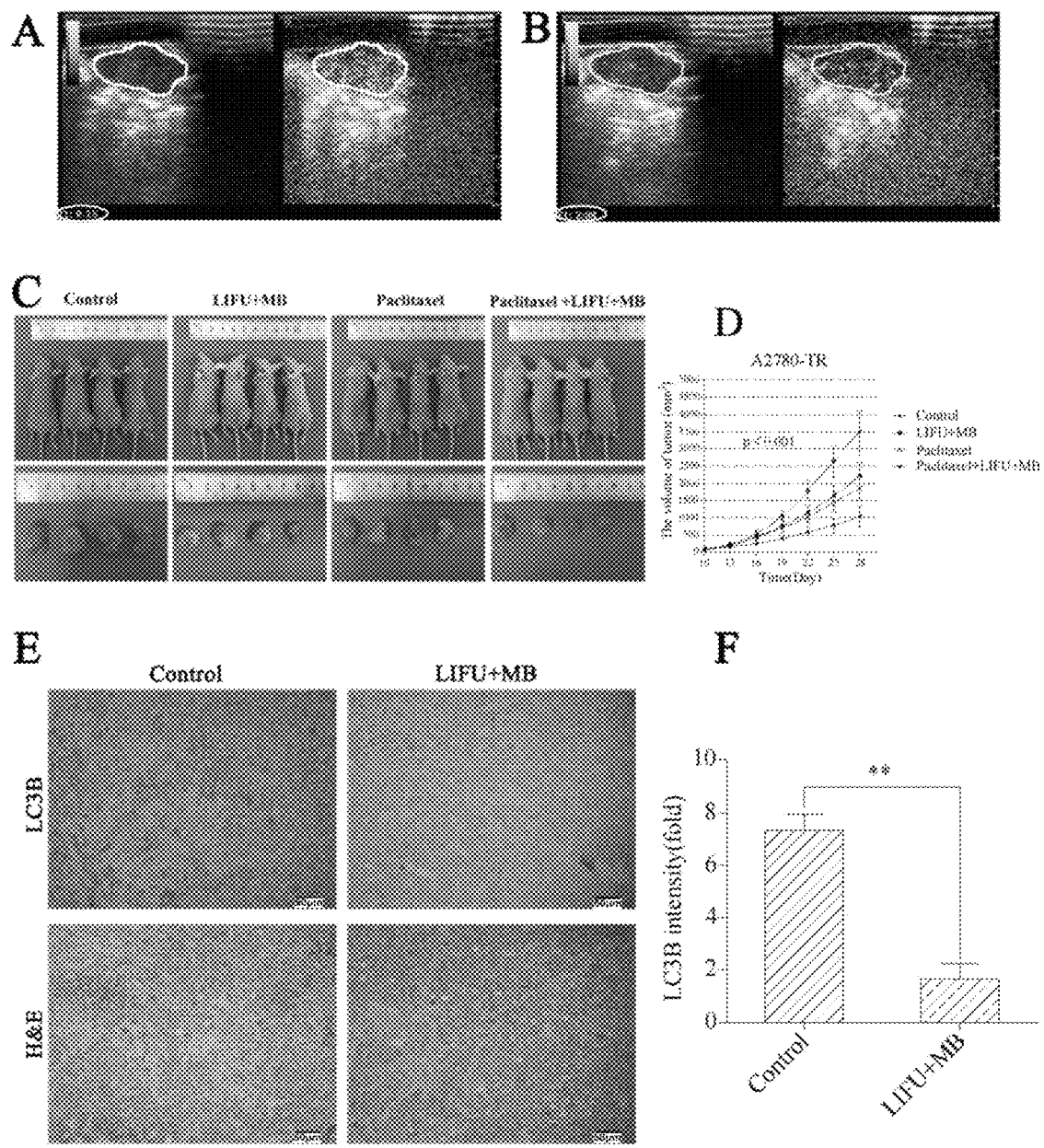
FIG. 7 is a schematic diagram of tumor growth curves of nude mice with negative tumors with different treatments according to the example of the present disclosure.

At present, there is no clear definition for the selection of LIFU energy. It is generally believed that ultrasound acoustic pressure greater than 1 MPa will cause cell death, blood vessel rupture and even intratumor hemorrhage. In the study of the present disclosure, different low acoustic pressure (0.12 MPa, 0.17 MPa, 0.21 MPa, 0.24 MPa, and 0.27 MPa), duty cycle (10%, 20%, 30%, 40%, and 50%), irradiation time (1 min, 2 min, 3 min, 4 min, and 5 min), and MB dose (1:1, 5:1, 10:1, 15:1, and 20:1) are applied to the epithelial ovarian cancer cell SKOV3 to observe instantaneous apoptosis of the cell. As shown in FIG. 3, instantaneous apoptosis rates of SKOV3 cells in the blank control group and after treatment with different ultrasound energies (0.12 MPa, 0.17 MPa, 0.21 MPa, 0.24 MPa, and 0.27 MPa) are detected by flow cytometry. There is no significant difference between the 0.12 MPa, 0.17 MPa, and 0.21 MPa irradiation treatments and the control group, and the instantaneous apoptosis rate of cells increases after 0.24 MPa and 0.27 MPa irradiation, showing the relationship between the instantaneous apoptosis rate of cells after treatment and the ultrasound dose. Finally, an ultrasound irradiation resonance frequency of 1.18 MHz, an acoustic pressure of 0.21 MPa, a duty cycle of 20%, an MB to cell ratio of 10:1, and an ultrasound irradiation time of 3 min are selected as ideal experimental parameters. At this time, the cells do not die immediately after irradiation, but the cell migration ability is weakened (FIG. 5), so the parameters are used for experimental study to increase the experimental safety. Through studies in animals, it is found that after ultrasound MB treatment (100 μl of MB/nude mouse, irradiation time of 3 min, once every three days for 2 weeks), there is no skin ulceration and necrosis on the tumor surface of nude mice through observation. Finally, the vital organs, the heart, liver, spleen, lung and kidney, of the nude mice in the control group and the treatment group are taken out for examination, and there is no obvious damage to vital organs (FIG. 7). Compared with literature reports, the ultrasound parameter selection is lower or similar to that reported in previous studies, so the system has a high safety factor if it is converted to clinical use.

As shown in FIG. 5 to FIG. 9, various control experiments can be conducted using the preferred values in Example 1, as described below.

Figure 5:
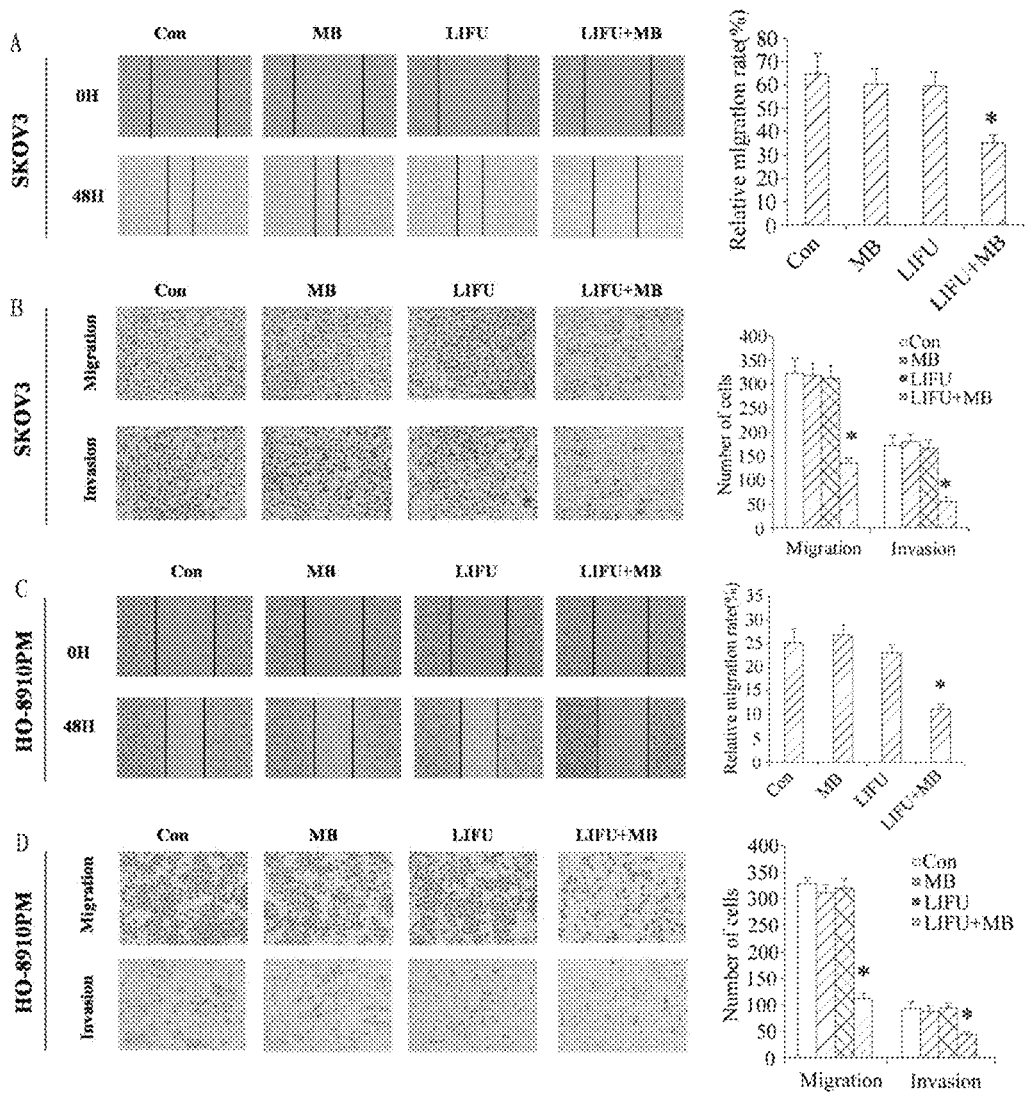
FIG. 5 is a schematic diagram of invasive and metastatic ability of cells after different treatments for 48 h according to the example of the present disclosure.
Figure 5:
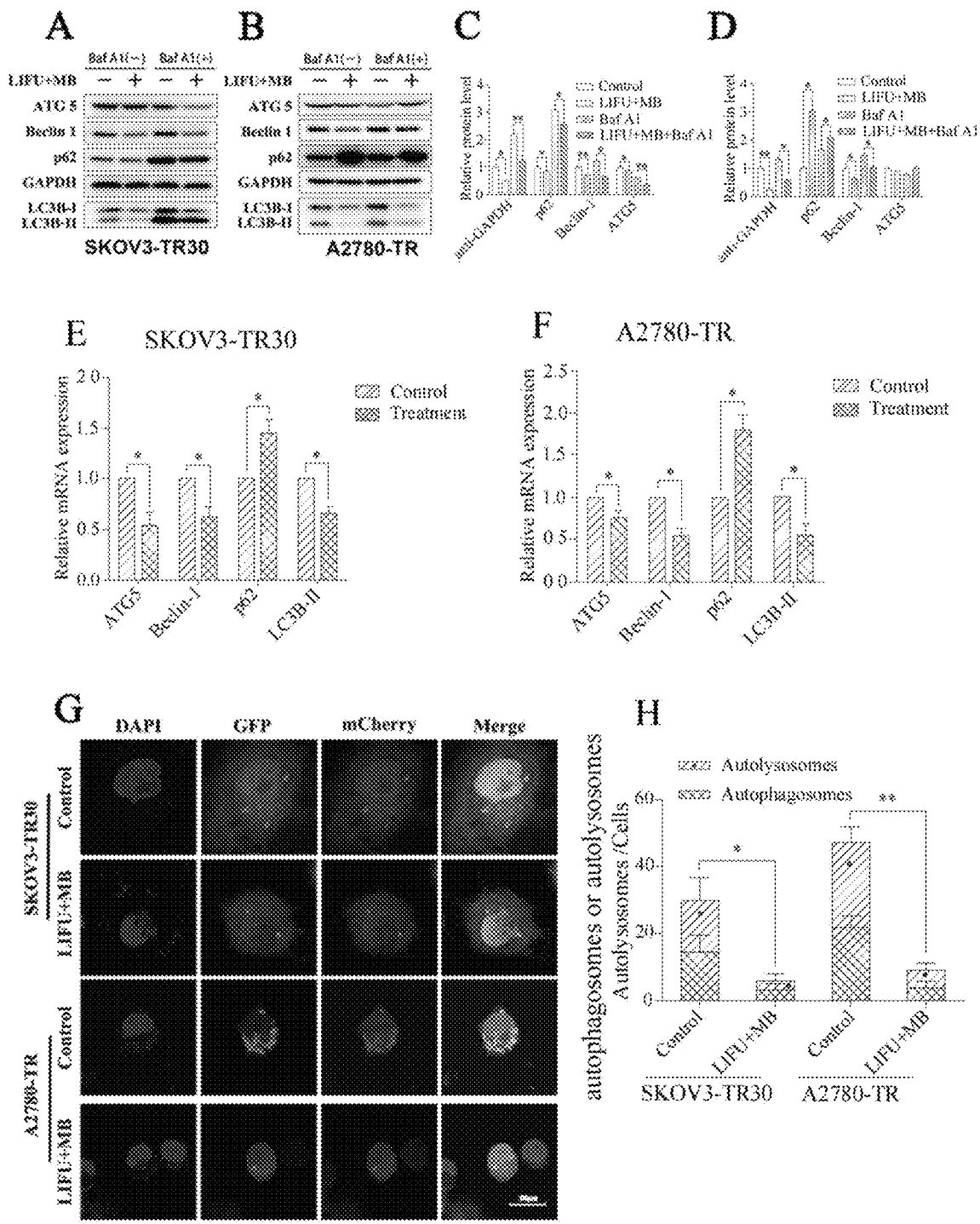

As shown in FIG. 5, migration and invasion abilities of ovarian cancer cells SKOV3 and HO-8910PM in the blank control group and the LIFU+MB group are compared. Characterization techniques include wound healing and transwell. (A) The scratch test of SKOV3 cells after LIFU+MB treatment for 48 h shows that the cell repair ability is weakened. (B) Transwell shows that the migration and invasion abilities are significantly reduced after LIFU+MB treatment for 24 h. (C, D) HO-8910PM cells show consistent results.

Figure 6:
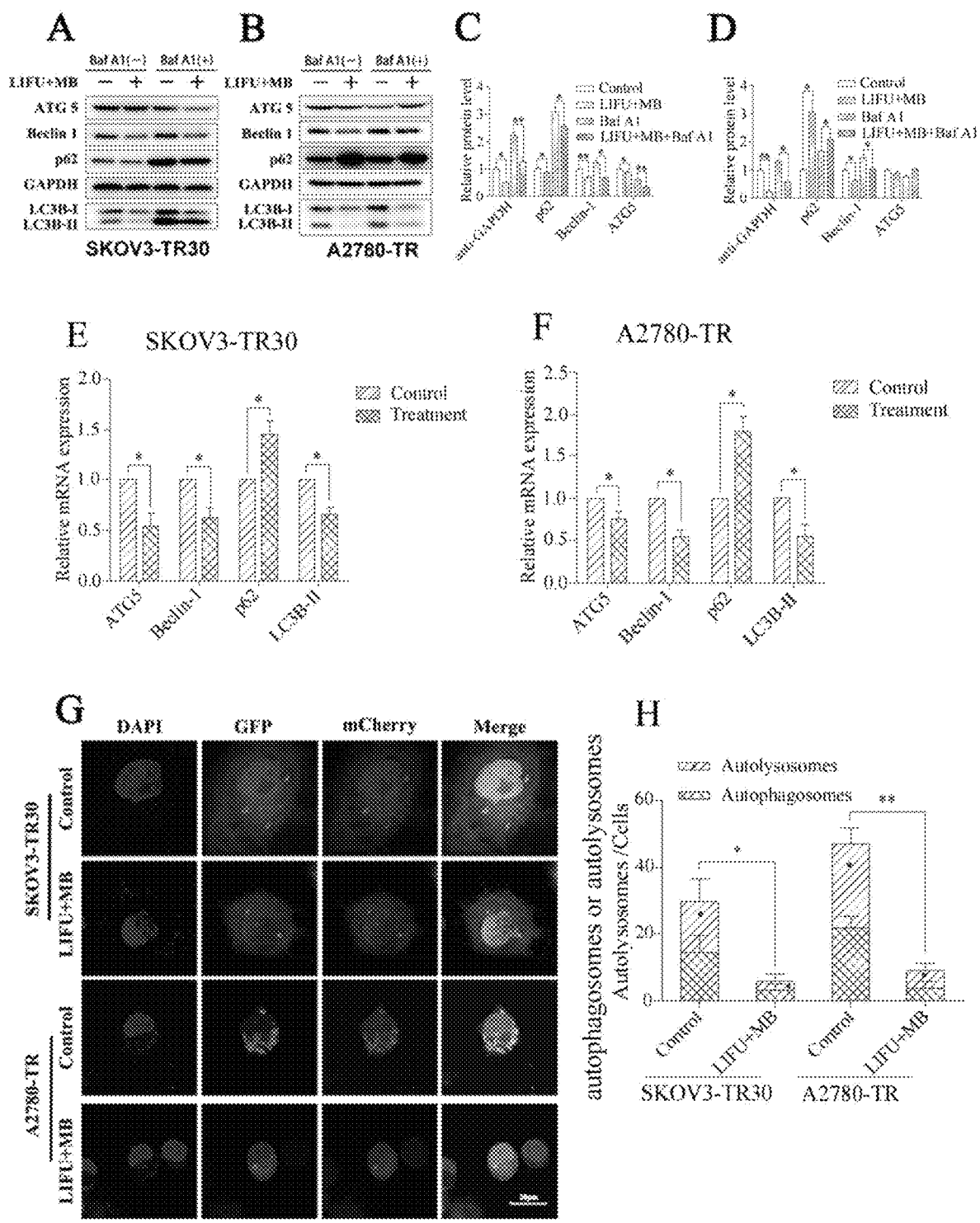
FIG. 6 is a schematic diagram of a level of autophagy of cells after different treatments for 24 h according to the example of the present disclosure.
Figure 6:
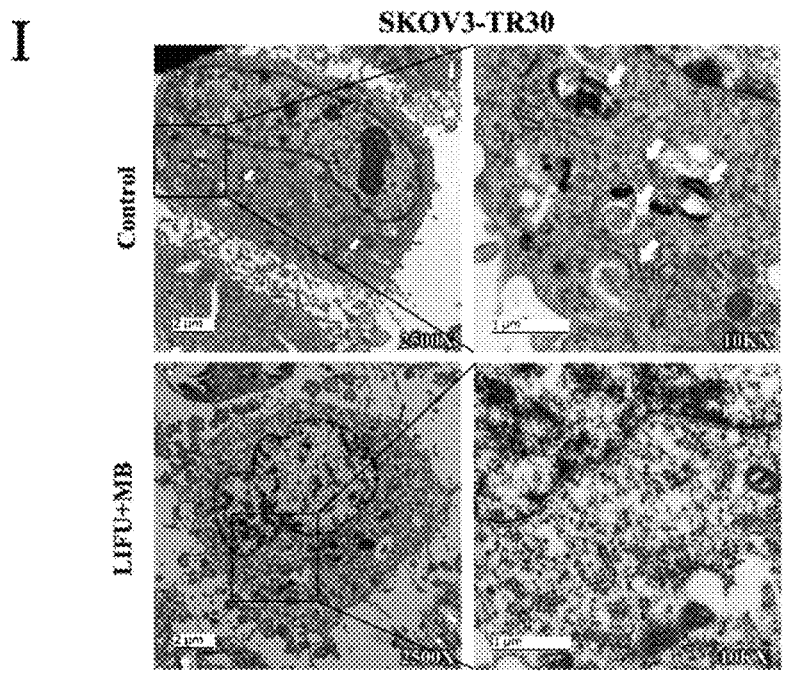
Figure 6:
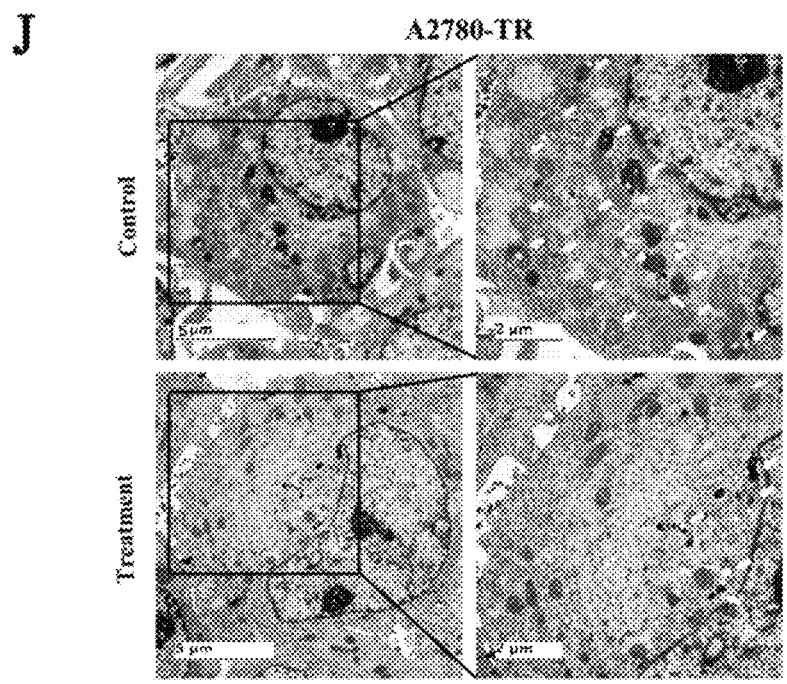
Figure 6:
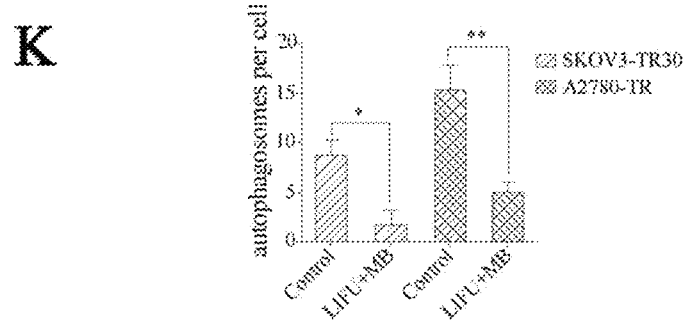

As shown in FIG. 6, the autophagy levels of the paclitaxel-resistant ovarian cancer cells A2780-TR and SKOV3-TR in the blank control group and the LIFU+MB group are compared, and the autophagy level changes are observed with the BafA1 group with the addition of the autophagy inhibitor. Characterization techniques include flow cytometry, fibered confocal fluorescence microscopy (FCFM), transmission electron microscopy (TEM), and western blot. (A-D) Western blot shows the expression of autophagy-related proteins in two-cell LIFU+MB group and the changes and quantitative analysis after addition of the autophagy inhibitor. (E, F) Autophagy-related protein levels in two-cell LIFU+MB group and blank control group by quantitative polymerase chain reaction (qPCR) are shown. (G, H) The number and counting analysis of autophagic vesicles in the two-cell LIFU+MB group and blank control group by FCFM are shown. (I-K) TEM shows the autophagic vesicles and counting analysis in the two-cell LIFU+MB group and blank control group.

Combined with the cell experimental study of the ultrasound therapy system of the present disclosure, the results show cell cycle arrest, filopodia reduction and arrangement disorder, invasive ability weakening, and autophagy-related protein expression weakening after LIFU+MB treatment. Furthermore, the analysis of transcriptome sequencing technology shows that LIFU+MB causes changes in the expression levels of various molecules, including autophagy-related molecules such as Atg5, cytoskeleton-related molecules such as CLASP1, tumor cell division and proliferation-related molecules such as NDC80, MAPK, and EGR1, and cell cycle-related molecules such as SMC3. Therefore, the biological effects caused by LIFU+MB are diverse.

FIG. 7 shows the experiment of paclitaxel-resistant ovarian cancer subcutaneous transplanted tumor in nude mice. (A, B) MB is injected into the tail vein, and the subcutaneous transplanted tumor is developed in vivo. (C, D) The tumor growth of nude mice treated with different treatments shows that the tumor growth rate of the Pacilitaxel+LIFU+MB treatment group is significantly lower than that of other groups. (E, F) The expression of autophagy-related protein LC3II is down-regulated by pathological sections of the tumor.

Figure 8:
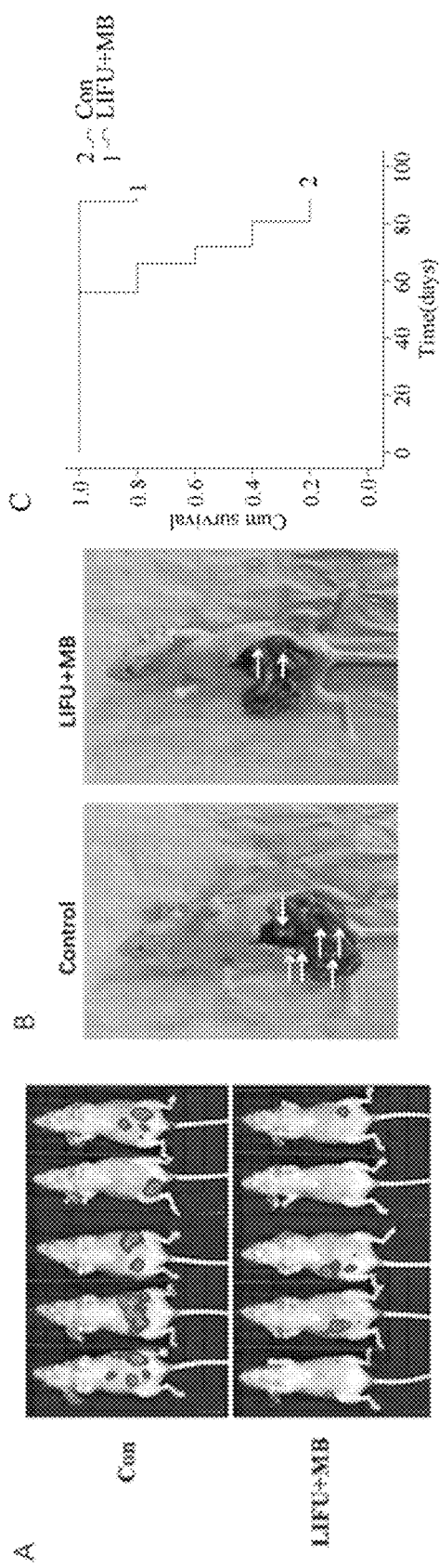
FIG. 8 is a schematic diagram of tumor metastasis and survival rates of nude mice with negative tumors with different treatments according to the example of the present disclosure.

As shown in FIG. 8, in the ovarian cancer metastasis model, the abdominal cavity of nude mice is inoculated with blank control and LIFU+MB irradiated ovarian cancer SKOV3 cells. (A) In vivo imaging of small animals shows the distribution of lesions. (B) Abdominal invasion and metastasis are observed after dissection one month later (the arrow points to tumor foci). (C) The survival curve shows that the survival time of the LIFU+MB group is significantly prolonged.

Figure 9:
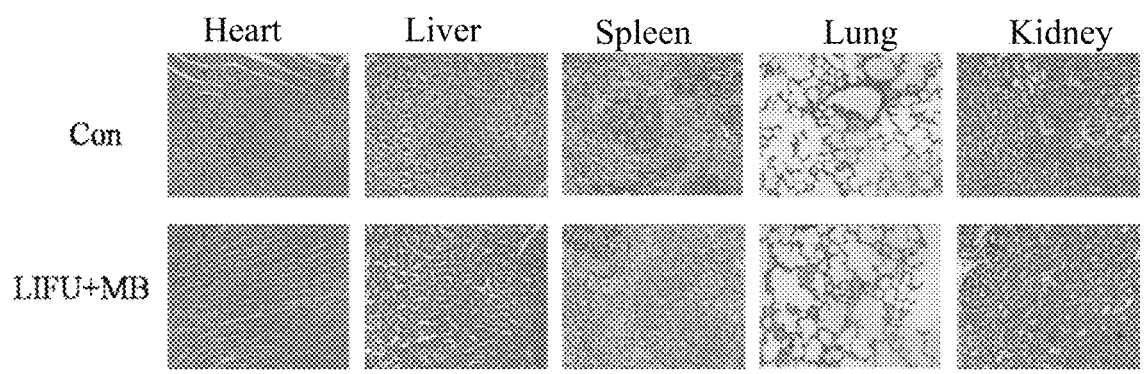
FIG. 9 is a histopathological diagram of important organs of nude mice with negative tumors with different treatments according to the example of the present disclosure.

As shown in FIG. 9, the effect on important organs is shown after LIFU+MB irradiation on subcutaneous transplanted tumor in nude mice. Through histological section observation, compared with the blank control group, there is no significant difference (200-fold) in cell morphology between the two groups.

Combined with the animal experimental study of the ultrasound therapy system of the present disclosure, the results show that after LIFU+MB treatment, tumor growth is inhibited, metastatic lesions are reduced, and the expression of related proteins in tumor tissue pathological sections is changed (such as the down-regulation of autophagy protein levels). In addition, there is no pathologically visible damage to important organs. Therefore, LIFU+MB in vivo therapy is effective and safe.

Example 5

The present example and Example 1 belong to the same inventive concept. As shown in FIG. 1, the example of the present disclosure provides a dose control method, including the following steps.

A first ultrasound irradiation device is driven to generate multiple groups of ultrasound irradiation doses, and ultrasound irradiation is conducted on a cell culture device with multiple groups of abnormally proliferating living cells. Each group of ultrasound irradiation dose is applied to at least one group of abnormally proliferating living cells.

Performance characteristic data of living cells in the cell culture device is obtained.

An ultrasound irradiation dose corresponding to at least one group of abnormally proliferating living cells with a cell target characteristic characterization is determined as a target ultrasound irradiation dose according to the performance characteristic data.

A second ultrasound irradiation device is driven to conduct ultrasound irradiation of the target ultrasound irradiation dose on a living organism with abnormal proliferation.

In some specific implementations, prior to the ultrasound irradiation on the cell culture device with the multiple groups of abnormally proliferating living cells, the method includes the following step.

Multiple groups of MB doses are applied to the multiple groups of abnormally proliferating living cells. Each group of MB dose is applied to at least one group of abnormally proliferating living cells from a selected MB injection group of living cells in the cell culture device.

In some specific implementations, prior to the ultrasound irradiation of the target ultrasound irradiation dose on the living organism with abnormal proliferation, the method includes the following step.

An MB dose corresponding to the at least one group of abnormally proliferating living cells with the cell target characteristic characterization is determined as a target MB dose.

Prior to the ultrasound irradiation of the target ultrasound irradiation dose on the living organism with abnormal proliferation, the method includes the following step.

The target MB dose is applied to the living organism with abnormal proliferation.

In some specific implementations, prior to the ultrasound irradiation of the target ultrasound irradiation dose on the living organism with abnormal proliferation, the method includes the following step.

A preset MB dose is applied to the living organism with abnormal proliferation.

In some specific implementations, before the target ultrasound irradiation dose is determined according to the performance characteristic data, the method includes the following step.

It is determined that at least one of the performance characteristic data has a cell target characteristic characterization. The cell target characteristic characterization is a relative previous state in the performance characteristic data, at least movement of living cells is significantly slowed down in a current state, and the cells are apoptotic immediately after a current group of ultrasound irradiation dose is applied or after the ultrasound irradiation is stopped.

In some specific implementations, before the target ultrasound irradiation dose is determined according to the performance characteristic data, the method includes the following step.

It is determined that at least one of the performance characteristic data has a cell target characteristic characterization. The cell target characteristic characterization is a relative previous state in the performance characteristic data, at least movement of living cells is significantly slowed down in a current state, and the cells remain viable within a predetermined time range after a current group of ultrasound irradiation dose is applied or after the ultrasound irradiation is stopped.

Example 6

Based on Examples 1 and 5, the example of the present disclosure provides dose control equipment, including: at least one processor, and a memory.

The at least one processor is included.

The memory is connected to the at least one processor.

The memory stores an instruction executable by the at least one processor, and the at least one processor executes the instruction stored in the memory to implement the method described above.

Example 7

Based on Examples 1 and 5, the example of the present disclosure provides a computer-readable storage medium storing a computer instruction. When the computer instruction runs on a computer, the computer is enabled to execute the method described above.

The foregoing describes optional implementations of the examples of the present disclosure in detail with reference to the accompanying drawings. However, the examples of the present disclosure are not limited to the specific details in the foregoing implementations. Within the scope of the technical concept of the examples of the present disclosure, various simple variations can be made to the technical solutions in the examples of the present disclosure. These simple variations all fall within the protection scope of the examples of the present disclosure.

In addition, it should be noted that various specific technical features described in the foregoing examples can be combined in any suitable manner, provided that there is no contradiction. To avoid unnecessary repetition, various possible combinations are not separately described in the examples of the present disclosure.

A person skilled in the art can understand that all or some of the steps for implementing the method in the foregoing examples can be completed by a program instructing relevant hardware. The program is stored in a storage medium, and includes a plurality of instructions to enable a single chip microcomputer, a chip, or a processor to perform all or some of the steps in the method described in each example of the present disclosure. The foregoing storage medium includes any medium that can store a program code, such as a universal serial bus (USB) flash disk, a mobile hard disk, a read-only memory (ROM), a random access memory (RAM), a magnetic disk, or an optical disk. In addition, various different examples of the present disclosure can also be arbitrarily combined, provided that the combinations do not violate the idea of the examples of the present disclosure. The combinations should also be regarded as the content disclosed in the examples of the present disclosure.

What is claimed is:

1. An ultrasound therapy system, comprising:
    a control device;
    a first ultrasound irradiation device configured to generate multiple groups of ultrasound irradiation doses driven by the control device and conduct ultrasound irradiation on a cell culture device with multiple groups of abnormally proliferating living cells, wherein each group of ultrasound irradiation dose is applied to at least one group of abnormally proliferating living cells;
    a characterization image capture device configured to capture performance characteristic data of living cells in the cell culture device, wherein
    the control device is further configured to determine an ultrasound irradiation dose corresponding to at least one group of abnormally proliferating living cells with a cell target characteristic characterization as a target ultrasound irradiation dose according to the performance characteristic data; and
    a second ultrasound irradiation device configured to conduct ultrasound irradiation of the target ultrasound irradiation dose on a living organism with abnormal proliferation, and conduct animal experiments based on cell experiments, wherein
    the ultrasound therapy system further comprises:
    a microbubble (MB) injection device configured to apply multiple groups of MB doses to the multiple groups of abnormally proliferating living cells prior to the ultrasound irradiation on the cell culture device with the multiple groups of abnormally proliferating living cells, wherein each group of MB dose is applied to at least one group of abnormally proliferating living cells in the cell culture device, wherein
    the control device is further configured to determine an MB dose corresponding to the at least one group of abnormally proliferating living cells with the cell target characteristic characterization as a target MB cose prior to the ultrasound irradiation of the target ultrasound irradiation dose on the living organism with abnormal proliferation; and
    the MB injection device is further configured to apply the target MB dose to the living organism with abnormal proliferation prior to the ultrasound irradiation of the target ultrasound irradiation dose on the living organism with abnormal proliferation,
    wherein the cell target characteristic characterization comprises weakened cell migration ability without immediate cell death; and the living organism with abnormal proliferation is an animal body transplanted with cancer cells.

2. The ultrasound therapy system according to claim 1, wherein
    the control device is provided with a parameter set configured to form any ultrasound irradiation dose; and the first ultrasound irradiation device is configured to generate the multiple groups of ultrasound irradiation doses driven by the control device according to the parameter set, wherein any two groups of parameters in the parameter set are different.

3. The ultrasound therapy system according to claim 2, wherein the control device is further configured to determine a group of parameters generating the target ultrasound irradiation dose as target parameters according to the target ultrasound irradiation dose;

the control device is further configured to modify the target parameters to modified target parameters of the second ultrasound irradiation device; and the second ultrasound irradiation device is configured to generate the target ultrasound irradiation dose driven by the control device according to the modified target parameters, and conduct ultrasound irradiation on the living organism with abnormal proliferation.

4. The ultrasound therapy system according to claim 3, wherein the group of parameters each comprises an ultrasound irradiation resonance frequency, an acoustic pressure, an acoustic intensity, a drive signal duty cycle, an MB dose, and an ultrasound irradiation time.

5. The ultrasound therapy system according to claim 1, wherein the first ultrasound irradiation device and the second ultrasound irradiation device each has a focused ultrasound transducer; and a maximum output ultrasound irradiation dose of the focused ultrasound transducer is configured to be less than or equal to an upper dose limit, wherein when the focused ultrasound transducer outputs the upper dose limit to egg white liquid or gel mixed with protein, the egg white liquid or the gel just produces a biological focal region.

6. The ultrasound therapy system according to claim 5, wherein a propagation coupling medium from the focused ultrasound transducer to the cell culture device in the first ultrasound irradiation device is degassed water or a liquid coupling medium; and a propagation coupling medium from the focused ultrasound transducer to the living organism in the second ultrasound irradiation device is degassed water, an acoustic coupling agent, or a liquid coupling medium.

7. The ultrasound therapy system according to claim 1, wherein a focal region of the first ultrasound irradiation device has a same or approximately same size as a focal region of the second ultrasound irradiation device.

\* \* \* \* \*